(12) United States Patent
Maass Sepúlveda et al.

(10) Patent No.: US 7,853,408 B2
(45) Date of Patent: Dec. 14, 2010

(54) METHOD FOR THE DESIGN OF OLIGONUCLEOTIDES FOR MOLECULAR BIOLOGY TECHNIQUES

(75) Inventors: Alejandro Eduardo Maass Sepúlveda, Santiago (CL); Andrés Octavio Aravena Duarte, Santiago (CL); Mauricio Alejandro Gonzalez Canales, Santiago (CL); Servet Martinez Aguilera, Santiago (CL); Pilar Angélica Parada Valdecantos, Santiago (CL); Katia Nicole Ehrenfeld Stolzenbach, Santiago (CL)

(73) Assignee: Biosigma S.A., Colina (CL)

( * ) Notice: Subject to any disclaimer, the term of this patent is extended or adjusted under 35 U.S.C. 154(b) by 1056 days.

(21) Appl. No.: 11/506,089

(22) Filed: Aug. 17, 2006

(65) Prior Publication Data

US 2007/0059743 A1  Mar. 15, 2007

(30) Foreign Application Priority Data

Aug. 17, 2005 (CL) .................................. 2102-2005

(51) Int. Cl.
*G06F 7/00* (2006.01)
(52) U.S. Cl. ............................. 702/19; 702/20; 703/11; 435/6; 536/24.5
(58) Field of Classification Search ....................... None
See application file for complete search history.

(56) References Cited

U.S. PATENT DOCUMENTS

2003/0097223 A1   5/2003   Nakae et al.

OTHER PUBLICATIONS

Gordon et al. 2004 Nucleic Acids Research vol. 32 No. 17, e133.*
Benson et al. "GenBank." *Nucleic Acids Research*. vol. 25. No. 1. 1997. pp. 1-6.
Bommarito et al. "Thermodynamic parameters for DNA sequences with dangling ends." *Nucleic Acids Research*. vol. 28. No. 9. 2000. pp. 1929-1934.
Le Novere. "MELTING, computing the melting temperature of nucleic acid duplex." *Bioinformatics Applications Not.* vol. 17. No. 12. 2001. pp. 1226-1227.
Mathews et al. "Expanded Sequence Dependence of Thermodynamic Parameters Improves Prediction of RNA Secondary Structure." *J. Mol. Biol.* vol. 288. 1999. pp. 911-940.
Needleman et al. "A General Method Applicable to the Search for Similarities in the Amino Acid Sequence of Two Proteins." *J. Mol. Biol.* vol. 48. 1970. pp. 443-453.
Rozen et al. "Primer3 on the WWW for General Users and for Biologist Programmers." Krawetz S. Misener S (eds) *Bioinformatics Methods*. 2000. pp. 365-386.
Thompson et al. "CLUSTAL W: improving the sensitivity of progressive multiple sequence alignment through sequence weighting, position-specific gap penalties and weight martrix choice." *Nucleic Acids Research*. vol. 22. No. 22. 1994. pp. 4673-4680.
Zuker. "Mfold web server for nucleic acid folding and hybridization prediction." *Nucleic Acids Research*. vol. 31. No. 13. 2003. pp. 3406-3415.
Wang et al. "A PCR primer bank for quantitative gene expression analysis." *Nucleic Acids Research*, vol. 31, No. 24. 2003. pp. 1-8.
Hofacker et al. "Fast Folding and Comparison of RNA Secondary Structures." *Monatsch. Chem Chem. Monthly*. vol. 125, 1994. pp. 167-188.

* cited by examiner

*Primary Examiner*—Mary K Zeman
(74) *Attorney, Agent, or Firm*—Merchant & Gould P.C.

(57) ABSTRACT

A method of designing oligonucleotides useful in molecular biology techniques as PCR primers or in other techniques as identification and/or quantification probes is disclosed. The method permits designing specific oligonucleotides for the identification of a determined sequence in a metagenomic sample. The method includes selecting or constructing a database of reference sequences, selecting a subset of sequences belonging to target organisms, selecting candidate oligonucleotides from such sequences, depurating these candidate oligonucleotides according to hybridization specificity and thermodynamic stability criteria, obtaining a list of designed oligonucleotides that fulfill the hybridization specificity and thermodynamic stability criteria, producing materially by chemical synthesis the designed oligonucleotides, and selecting the oligonucleotides which comply with the requirements of the desired process.

12 Claims, 1 Drawing Sheet

METHOD FOR THE DESIGN OF OLIGONUCLEOTIDES FOR MOLECULAR BIOLOGY TECHNIQUES

FIELD OF THE INVENTION

The present invention discloses a method for the design of oligonucleotides useful in molecular biology techniques as PCR primers or in other techniques as identification and/or quantification probes. Specially, a method is disclosed to design specific oligonucleotides for the identification of a determined sequence in a metagenomic sample.

BACKGROUND OF THE INVENTION

Many methods in molecular biology require the use of short DNA sequences (oligonucleotides) satisfying given physicochemical and biological requirements to assess the presence of a certain organism or group of organisms. Among these methods, fluorescent in situ hybridization (FISH), denaturing gradient gel electrophoresis (DGGE), conjugation with specific markers, like detection or quantification probes for certain microorganisms, genes or sequences, and polymerase chain reaction (PCR), where two oligonucleotides are used as primers for the reaction, could be mentioned. This invention could be applied in said cases or in other cases wherein specific oligonucleotides are required.

Usually, oligonucleotides are artificially synthesized according to the description of their composing bases. The determination of the specific sequences that are suitable for each particular procedure is called "oligonucleotide design". According to the involved procedure, certain thermodynamic restrictions could limit the set of valid oligonucleotides. Oligonucleotides resulting from this design procedure will be completely determined by the nucleotide sequences used in their synthesis, which could be characterized as words having finite length in the alphabet {A, C, T, G}.

Traditional oligonucleotide design methods, among which Primer3 (Rozen S., Skaletsky, H. (2000). Primer3 on the WWW for general users and for biologist programmers. In: Krawetz S, Misener S (eds) Bioinformatics Methods and Protocols: Methods in Molecular Biology. Humana Press, Totowa, N.J., pp 365-386) can be mentioned, allow the design of oligonucleotides pairs or primers for PCR amplification, validating a series of thermodynamic requirements. However, these methods only allow the design of oligonucleotides for a particular sequence, not considering the case where many sequences from different organisms are to be recognized. The traditionally used method in this case requires performing a multiple alignment of all the sequences that are to be recognized, by means of a computer program as CLUSTALW (Higgins D., Thompson J., Gibson T. (1994). CLUSTAL W: improving the sensitivity of progressive multiple sequence alignment through sequence weighting, position-specific gap penalties and weight matrix choice. Nucleic Acids Res. 22:4673-4680). This alignment allows the determination of conserved regions among all the sequences to be recognized and therefore the design of oligonucleotides within these regions. However, the performance of these alignments is expensive and could be prohibitive when the number of sequences is large. Moreover, multiple alignments require the determination of penalty parameters derived from some evolutionary model of the sequences. The result depends on the values chosen for these penalties and may not be robust when confronted to small changes in these values.

Among other methods for oligonucleotide design that have been developed in the last years, document US2003097223 (Nakae & Ihara, 22/05/2003) could be mentioned, for instance, which protects a new primer design method. This method automatically designs primer pairs and then these primer pairs are selected according to certain requirements, namely oligonucleotide length, GC content percentage and Tm (melting temperature). Besides the basic aspects in primer design, well-known for someone skilled in the art, the method of the present invention considers a thermodynamic analysis of the designed primers, which adds an advantage over the method described in US2003097223 as the stability of the designed primers is guaranteed, improving the success probabilities of the use of said primers. Another different aspect between the former document and the invention herein disclosed is the fact that said document points to the finding of primers useful for many exons of a genome, whereas in one aspect of the invention all the microorganisms belonging to certain taxon are to be amplified; this fact constitutes a difference by itself, but the strategy used in both cases to find primers or oligonucleotides that could recognize more than one template is also different in both cases: in document US2003097223 a plurality of primers is designed (indicated as step 701) using bioinformatics means from a data base comprising different exons (step 700), and then PCR amplified DNA fragments are analyzed together with the designed primers, and primers amplifying target exons are empirically determined. Inversely, in the present invention primers present in the maximum number of target sequences are identified from the design database (which includes the target sequences) and primers to be synthesized and used are chosen based on this information.

Another document belonging to a related field in the art is the paper of Wang and Seed: "A PCR primer bank for quantitative gene expression analysis", Nucleic Acids Research, 2003, vol. 31, No. 24 e154, where an algorithm is validated for the identification of specific transcription primers for PCR; the authors have created an online database with primers that fulfill said requirements for human and mice genes. The algorithm described by Wang and Seed significantly differs form the method proposed in the present invention, firstly because it does not contemplate the possibility of choosing an oligonucleotide or a primer pair common to a determined taxon, but specific primers are chosen for only one target sequence, and secondly because in the oligonucleotide selection procedure $\Delta G$ is evaluated only for the last 5 residues at the 3' end of the molecule and the candidate is rejected when such value is less than −9 kcal/mole. In the present invention, $\Delta G$ is evaluated for all the candidate oligonucleotides and the selection criteria is much stringent, as preferentially only oligonucleotides having $\Delta Gh_{min}$ equal to −1.5 kcal/mole ($\Delta G$ for hairpin formation) are selected. In order to predict the formation of hairpins in the referred paper, sequence auto-complementarity is evaluated and only 5 non-contiguous matches are allowed. In the same way, to avoid the formation of primer dimers the presence of complementary sequences in 4 residues at the 3' end of the molecule in the same primer (to avoid dimers) and in the other primer (to avoid cross-reactivity) is evaluated. In the present invention, secondary structure formation is faced in a different and more efficient way than the simple sequence complementarity comparison; in this case, differences in Gibbs free energies are evaluated for all possible conformations and the probability of each selected oligonucleotide to form secondary structures is determined based on the most stable conformation.

As can be appreciated, the method of the invention shows indisputable technical advantages over other existent methods in the state of the art.

In summary, up to this date no oligonucleotide design method has been disclosed being fast and economical and allowing the design of specific oligonucleotides for a target sequence when said sequence is part of a metagenomic sample or allowing the design of oligonucleotides that simultaneously recognize various sequences belonging to different organisms.

In this disclosure, said problems of the existing technique have been solved, creating a method for the design of specific oligonucleotides for a given sequence or group of sequences, that considers not only the information of the genetic material to be identified but also the information of all the genetic material that could be present in a metagenomic sample over which the method will be applied.

Another common problem in the field of oligonucleotide design is the fact that even when an oligonucleotide meeting the required specificity could be available, in practice of molecular biology procedures said oligonucleotide is not efficient. Explanations for this inefficiency are formation of secondary structures within the oligonucleotide sequence (hairpins) or auto-hybridization, which decreases the active concentration of the oligonucleotide in the reaction mix. In the case of PCR technique, where an oligonucleotide pair is simultaneously used, a cross-hybridization between both oligonucleotides could be possible, besides auto-hybridization and hairpin formation, which also sequesters oligonucleotides in the reaction mix and makes said reaction inefficient.

In order to overcome this technical problem, the method of the invention includes a step wherein the designed oligonucleotides are thermodynamically evaluated to discard formation of hairpins, auto-hybridization or cross-hybridization between two primers. For each of these situations, Gibbs free energy differences are calculated for all the possible conformations, the most stable conformation being selected; if said most stable conformation has a $\Delta G$ value less than a certain threshold, said oligonucleotide is discarded, thus guaranteeing the availability of the designed oligonucleotides.

Thus, the method of the present invention allows solving all the problems existing in the field of oligonucleotide design for Molecular Biology techniques.

SUMMARY OF THE INVENTION

As previously described, the present invention discloses a method that can be used to identify one DNA or RNA sequence or one specific group of DNA or RNA sequences from a complex biological sample.

Diverse molecular biology methods require the presence of short DNA sequences, called oligonucleotides, that are artificially synthesized from a description of their composing bases.

The oligonucleotide design method comprises the selection or construction of a database of reference sequences, the selection of a subset of sequences belonging to target organisms, the selection of candidate oligonucleotides from such sequences, the depuration of these candidate oligonucleotides according to hybridization specificity and thermodynamic stability criteria, which allows to obtain a list of designed oligonucleotides and, optionally, the sorting of such oligonucleotides according to their taxonomical specificity.

The extension of this method to the case in which oligonucleotides pairs are required is also disclosed, as could be the case of polymerase chain reaction (PCR) procedures. This method variant comprises the construction or selection of a database of reference sequences, the selection of a subset of sequences belonging to target organisms, the selection of two sets of candidate oligonucleotides from such sequences, the depuration of each set of candidate oligonucleotides according to hybridization specificity and thermodynamic stability criteria, the elaboration of a list of oligonucleotides pairs or primers formed by one element from each set that satisfy physical and thermodynamic requirements and the sorting of such oligonucleotides pairs according to taxonomical specificity.

DETAILED DESCRIPTION OF THE INVENTION

Figure 1:
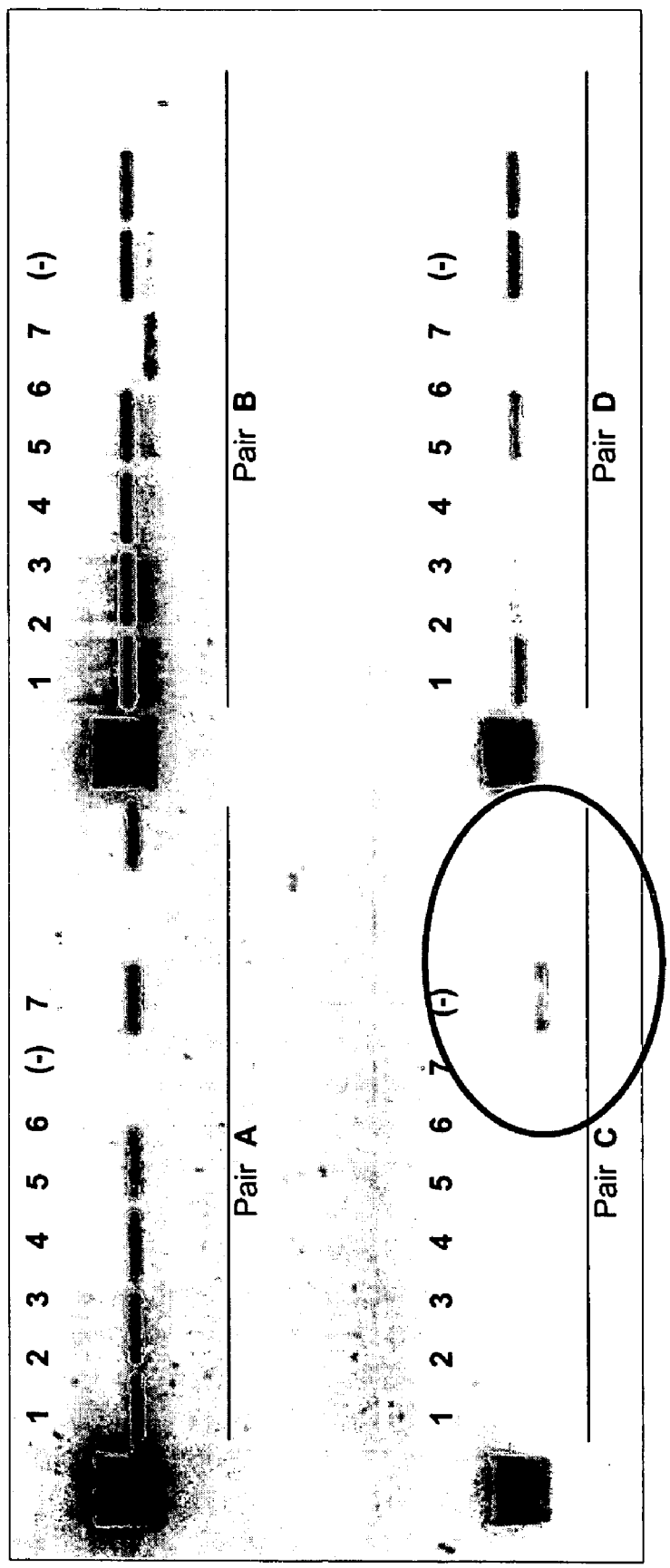
FIG. 1 shows the results of a PCR performed with oligonucleotides pairs or primers designed using the method of the invention to carry out a specific PCR for *A. thiooxidans* amplifying 16S rDNA from 5 samples of *A. ferrooxidans* and 2 samples of *A. thiooxidans*; the content of each lane is specified in the Examples section, in Table 5.

Oligonucleotide Design.

The method for the design of oligonucleotides herein described takes a database of DNA or RNA sequences as an input. Depending on experimental requirements being considered, these sequences may be complete genomes or fragments from each genome. For instance, all known sequences of a given gene or genomic region could be considered. In a preferred embodiment of the present invention, a database designed by us is considered, which contains all known sequences of gene 16S. A requirement to be met by the database under use is that every sequence must have been taxonomically classified. An example of database that can be used as input with the method of this invention is GenBank, from NCBI (Benson, D. A., Boguski, M. S., Lipman, D. J., Ostell, J. (1997). GenBank. Nucleic Acids Res. Jan 1; 25(1): 1-6). This selected or constructed database is called "evaluation database". From this database, the sequence subset corresponding to the organism(s) to be identified is extracted. This subset is called "design database".

In some cases, considering the fact that partial sequences of the target genes could be found in public databases, it is convenient to normalize the relative positions within each sequence, and so each sequence in the design database is optimally aligned to a reference sequence, which may be a gene that is homologous to the analyzed one, using the Needleman-Wunsch algorithm (Needleman, S. B., Wunsch, C. D. (1970). *A general method applicable to the search for similarities in the amino acid sequence of two proteins*. J Mol Biol. Mar; 48(3):443-53). In said case, these aligned sequences form the design database.

Once the design database has been defined, the oligonucleotide set therein contained is established. This oligonucleotide set is built considering each subsequence, hereinafter called 'words', that has a defined size (typically between 18 and 50 letters) and is contained in each subsequence and also in the subsequences that are complementary reverse to them. The words that are present more than once in some sequence are discarded, considering also a number of substitutions within the word, which typically could be up to 15% of the letters contained in the word. For instance, in a 20-letter word, 15% corresponds to 3 substitutions, so if a word having length 20 is coincident in 17 or more letters with another word of the same sequence, both words are discarded. This procedure is efficiently performed if the hereinbelow described algorithm is followed, taking as inputs the design database, the size of the oligonucleotides being designed (n) and the maximum number of allowed letter substitutions (u). The selection of candidate oligonucleotides is performed by taking into account all subsequences of defined length that are present in the target sequences and their corresponding reverse-complementary sequences.

reaction (PCR) or fluorescent in situ hybridization (FISH), a second validation should be performed, which requires the evaluation of the smallest Gibbs free energy of all the structures formed by two copies of the candidate oligonucleotide.

---

Algorithm 1

---

For each sequence $S_i$ in the design database
  Consider each word $P_{ij}$ being a previously unseen subsequence of $S_i$ with length n
  For each sequence $S_k$, $C_k$ is defined as the number of times the oligonucleotide appears within each candidate sequence, wherein subscript k is the sequence number.
    $C_k \leftarrow 0$
    For each word $P_{kl}$ being a subsequence of $S_k$ with length n
      If word $P_{kl}$ coincides with $P_{ij}$ in at least n-u letters
        $C_k \leftarrow C_k + 1$
      If word $P_{kl}$ coincides with $P_{ij}$ in exactly n letters
        Mark word $P_{kl}$ as previously seen
        Remember that $P_{ij}$ hybridizes with $S_k$ on strand +1
    For each word $P'_{kl}$ being a reverse-complementary sequence of $P_{kl}$
      If word $P'_{kl}$ coincides with $P_{ij}$ in at least n-u letters
        $C_k \leftarrow C_k + 1$
      If word $P'_{kl}$ coincides with $P_{ij}$ in exactly n letters
        Mark word $P_{kl}$ as previously seen
        Remember that $P_{ij}$ hybridizes with $S_k$ on strand −1
    If $C_k$ is greater than 1
      Mark word $P_{ij}$ as discarded
  If $P_{ij}$ is not discarded
    Print word $P_{ij}$ as oligonucleotide candidate on strand +1
  Consider each word $P'_{ij}$ being a previously unseen reverse-complementary sequence of $P_{ij}$
  For each sequence $S_k$
    $C_k \leftarrow 0$
    For each word $P_{kl}$ being a subsequence of $S_k$ with length n
      If word $P_{kl}$ coincides with $P'_{ij}$ in at least n-u letters
        $C_k \leftarrow C_k + 1$
      If word $P_{kl}$ coincides with $P'_{ij}$ in exactly n letters
        Mark word $P_{kl}$ as previously seen
        Remember that $P'_{ij}$ hybridizes with $S_k$ on strand +1
    For each word $P'_{kl}$ being a reverse-complementary sequence of $P_{kl}$
      If word $P'_{kl}$ coincides with $P'_{ij}$ in at least n-u letters
        $C_k \leftarrow C_k + 1$
      If word $P'_{kl}$ coincides with $P'_{ij}$ in exactly n letters
        Mark word $P'_{kl}$ as previously seen
        Remember that $P'_{ij}$ hybridizes with $S_k$ on strand −1
    If $C_k$ is greater than 1
      Mark word $P'_{ij}$ as discarded
  If $P'_{ij}$ is not discarded
    Print word $P'_{ij}$ as oligonucleotide candidate on strand −1

---

Each word or subsequence generated by the described algorithm is called "candidate oligonucleotide". In this first attempt a large quantity of candidate oligonucleotides is obtained, which are submitted to the selection criteria of the method.

These candidates are then evaluated by their thermodynamic stability. The first evaluation is the determination of the Gibbs free energy for the smallest energy secondary structure. This means that Gibbs free energy difference is calculated for all the spatial conformations where the oligonucleotide hybridizes with itself, until the structure with the smallest energy difference, i.e. the most stable structure, is found. If this value, which is called $\Delta Gh_{min}$ as it defines the Gibbs free energy difference for hairpin formation of the oligonucleotide, is smaller than a threshold value, defined in a first attempt as the best quartile, the candidate oligonucleotide is discarded. If it is desired to reduce even more the number of candidate oligonucleotides, a larger $\Delta Gh_{min}$ could be selected, which may be, e.g., −7 kcal/mole. The $\Delta Gh_{min}$ threshold value preferably used according to the invention is −1.5 kcal/mole.

For certain procedures where designed oligonucleotide concentration would be too high, as in polymerase chain reaction (PCR) or fluorescent in situ hybridization (FISH), a second validation should be performed, which requires the evaluation of the smallest Gibbs free energy of all the structures formed by two copies of the candidate oligonucleotide. Analogously, if this energy does not surpass a threshold value for $\Delta Gd_{min}$, which defines the Gibbs free energy difference for the formation of oligonucleotide dimers, the oligonucleotide is discarded. In a first approach, the threshold is defined as the best quartile and, if a stricter bound for the oligonucleotide number is desired, a larger $\Delta Gd_{min}$ can be selected. The $\Delta Gd_{min}$ threshold value preferentially used according to this invention is −7 kcal/mole.

Methods to calculate these minimal energies are well known and have been described in literature, for instance:

Bommarito S., Peyret N., SantaLucia J. Jr. (2000). *Thermodynamic parameters for DNA sequences with dangling ends*. Nucleic Acids Res. May 1; 28(9):1929-34. D. H. Mathews, J. Sabina, M. Zuker & D. H. Turner. (1999) *Expanded Sequence Dependence of Thermodynamic Parameters Improves Prediction of RNA Secondary Structure*. J. Mol. Biol. 288, 911-940.

M. Zuker. (2003) *Mfold web server for nucleic acid folding and hybridization prediction*. Nucleic Acids Res. 31 (13), 3406-15.

Ivo L. Hofacker, Walter Fontana, Peter F. Stadler, L. Sebastian Bonhoeffer, Manfred Tacker, and Peter Schuster (1994).

*Fast Folding and Comparison of RNA Secondary Structures. Monatsh. Chem.* 125: 167-188.

All the oligonucleotides that have not been discarded in the former stage are oligonucleotides designed by the method and are useful in molecular biology procedures.

Identification of Taxonomical Groups with Designed Oligonucleotides.

In identification procedures, it is desired to mark the presence of a specific taxonomical group in the sample. For this purpose, the evaluation database is analyzed looking for each oligonucleotide, registering the taxonomical group of the sequence in which the oligonucleotide appears. This operation generates, for each oligonucleotide, a table indicating the number of sequences belonging to each taxonomical group to which said oligonucleotide hybridizes. This table allows the calculation of two taxonomical specificity indexes given the target taxonomical group for each oligonucleotide, said indexes being described as follows:

Let N be the number of sequences belonging to the target taxonomical group that are present in the evaluation database. Let T be the number of sequences belonging to the target taxonomical group to which said oligonucleotide hybridizes; and let R be the total number of sequences to which said oligonucleotide hybridizes. We use "Sensitivity" to designate the percentage or ratio of target sequences effectively found. That is:

Sensitivity=T/N

Analogously, we use "Selectivity" to designate the percentage or ratio of found sequences belonging to the target group. That is:

Selectivity=T/R

For instance, if the target taxonomical group is *Escherichia coli*, there are N=80 sequences in the evaluation database belonging to this species, and the oligonucleotide hybridizes to R=120 sequences, of which T=60 belong to *E. coli*, then the Sensitivity of this oligonucleotide is Sensitivity=T/N=60/80=0.75

Whereas the Selectivity is

Selectivity=T/R=60/120=0.5

In other words, the oligonucleotide allows the identification of 75% of the sequences belonging to *E. coli*. Of all the recognized sequences, 50% belong to *E. coli*.

Most suitable oligonucleotides for identification procedures should simultaneously maximize both indexes. The following step in the method of this invention is the selection of the oligonucleotide with the largest Sensitivity and Selectivity, simultaneously. This can be achieved by, for example, obtaining the product of both indexes for each oligonucleotide and choosing the largest value thus obtained; this product is called "Rate".

The following algorithm describes the procedure to calculate these indexes for an oligonucleotide, represented as O, as a function of the number of letters forming O (represented by n) and the maximum number of permitted substitutions, represented by u:

---
Algorithm 2
---
Let be T ← 0
Let be N ← 0
Let be R ← 0

---
-continued
---
Algorithm 2
---
For each sequence $S_i$ in the reference database
   If $S_i$ belongs to the target taxonomical group
      N ← N+1
   For each word $P_{ij}$ being a subsequence of $S_i$ with length n
      If $P_{ij}$ coincides with O in more than n-u letters
         R ← R+1
         If $S_i$ belongs to the target taxonomical group
            T ← T+1
Finally,
   Sensitivity ← T/N
   Selectivity ← T/R
   Rate ← $T^2$/(N·R)

---

The oligonucleotides designed and selected according to this method are useful in molecular biology procedures intended to determine the presence of a target taxonomical group in a complex sample. Generally, they are produced by chemical synthesis and could be labeled by any known labeling technique, e.g. radioactive, fluorescent or chemiluminiscent labeling.

Design of Oligonucleotides Pairs or Primers.

Certain types of molecular biology procedures require the simultaneous presence of many different oligonucleotides. For instance, polymerase chain reaction (PCR) requires the presence of two oligonucleotides that satisfy certain requirements. The subject method of this invention is complemented in this case by the following steps.

Further to the abovementioned elements, this complementary stage requires the definition of a maximum and minimum size for the desired PCR product and a limit for the melting temperature (Tm) difference between both oligonucleotides.

To start, oligonucleotides designed according to Algorithm 1 are considered.

For each sequence in the design database, oligonucleotides pairs or primers formed by oligonucleotides that hybridize to the sequence are considered, in such a way that the first oligonucleotide hybridizes to the forward strand and the second oligonucleotide hybridizes to the reverse strand. The "amplification size" is calculated as the difference between the hybridization positions of the second oligonucleotide minus the first one. Pairs of oligonucleotides having amplification sizes outside the pre-established range are discarded.

For each oligonucleotide, Tm is calculated using the method described by Le Novére N. (2001). *MELTING, computing the melting temperature of nucleic acid duplex.* Bioinformatics. 2001 Dec; 17(12):1226-7.

Pairs of oligonucleotides having a melting temperature difference over the pre-established temperature difference, which is preferably less than 4° C., are discarded.

Once an oligonucleotide pair list fulfilling the established requirements is obtained using the described method, the thermodynamic stability of the oligonucleotide pair is evaluated by determining the minimal energy structure formed by both oligonucleotides when hybridizing each other. If this energy, which is called $\Delta Gx_{min}$ as it defines the Gibbs free energy difference for cross-hybridization between both oligonucleotides, is smaller than a threshold value, defined in a first attempt as the best quartile, the oligonucleotide is discarded. In all cases, such threshold should not be lower than −12 kcal/mole.

The method used to calculate $\Delta Gx_{min}$ is described in M. Zuker. (2003) *Mfold web server for nucleic acid folding and hybridization prediction.* Nucleic Acids Res. 31 (13), 3406-15.

Oligonucleotides pairs or primers that fulfill size restrictions for the amplification product, melting temperature difference restrictions and thermodynamic stability restrictions should be evaluated according to their taxonomical specificity. The abovementioned Selectivity and Sensitivity parameters are evaluated but for each oligonucleotide pair member. An oligonucleotide pair is considered to hybridize to a target sequence if both oligonucleotides hybridize to said sequence. That is, the set of sequences to which the oligonucleotide pair hybridizes is the intersection of the sets of sequences to which each oligonucleotide hybridizes.

Having been determined the set of sequences to which the oligonucleotide pair hybridizes, the corresponding Selectivity and Sensitivity indexes are calculated, and pairs that maximize both criteria are selected for the molecular biology procedure.

The following described algorithm allows the identification of oligonucleotides pairs or primers that satisfy the requirements described above. It should be taken into account that for each of them the strand to which it hybridizes (1 or −1) and the melting temperature, called Tm, has already been determined in the oligonucleotide design stage.

---
Algorithm 3
---

For each sequence $S_i$ in the design database
    For each oligonucleotide $F_{ij}$ that hybridizes to $S_i$ at position j of strand 1
        For each oligonucleotide $R_{ik}$ that hybridizes to $S_i$ at position k of strand −1
            Size ← k-j   (size of the amplified region)
            If Size is within the specified range
                If $Tm(F_{ij})$ is different from $Tm(R_{ik})$ in no more than 2 degrees
                ΔGd ← Heterodimer free energy
                If $\Delta Gd > \Delta Gd_{min}$
                    Let be T ← 0
                    Let be N ← 0
                    Let be R ← 0
                    For each sequence $S_m$ in the reference database
                        If $S_m$ belongs to the target taxonomical group
                            N ← N+1
                        If $S_m$ simultaneously contains $F_{ij}$ and $R_{ik}$
                            R ← R+1
                            If $S_m$ belongs to the target taxon
                                T ← T+1
                Sensitivity ← T/N
                Selectivity ← T/R
                Rate ← $T^2/(N \cdot R)$
                Print $F_{ij}$, $R_{ik}$, Sensitivity, Selectivity, Rate
The oligonucleotide pair that maximizes "Rate" is selected

---

The oligonucleotide pair that maximizes the "Rate" parameter is selected. The oligonucleotides pairs or primers designed and selected according to this method are useful in molecular biology procedures, such as PCR, intended to determine the presence of a target taxonomical group in a complex sample.

EXAMPLES

Example 1

Design of a Specific Oligonucleotide for Bacteria Belonging to *Leptospirillum* Genus.

A new database was obtained with data comprising only 16S sequences selected from the public NCBI GenBank database. This new database is the "evaluation database".

All sequences that come from bacteria belonging to *Leptospirillum* genus, 44 sequences in this case, were selected to be the "design database".

The set of 20-letter oligonucleotides that are present in each of the sequences was determined, discarding those sequences appearing more than once within each sequence, considering up to 3 substitutions, using Algorithm 1. These oligonucleotides are the "candidate oligonucleotides", which were evaluated according to their thermodynamic stability using the algorithm described in M. Zuker. (2003) Mfold web server for nucleic acid folding and hybridization prediction, Nucleic Acids Res. 31 (13), 3406-15. All candidate oligonucleotides with ΔGh values lower than −1.5 kcal/mole or with ΔGd values lower than −7 kcal/mole were discarded. This analysis provided a total of 14785 oligonucleotides that were present in at least one of the 44 sequences in the design database. None of them is present in all the design sequences. Oligonucleotides present in most of the sequences were considered. This reduced the list to 12 oligonucleotides, which are the oligonucleotides designed by the method and have the following structures:

Oligonucleotide 1:    TACAGACTCTTTACGCCCAG   (SEQ ID NO: 1)

Oligonucleotide 2:    CTACAGACTCTTTACGCCCA   (SEQ ID NO: 2)

Oligonucleotide 3:    CCTACAGACTCTTTACGCCC   (SEQ ID NO: 3)

Oligonucleotide 4:    ACCTACAGACTCTTTACGCC   (SEQ ID NO: 4)

Oligonucleotide 5:    CACCTACAGACTCTTTACGC   (SEQ ID NO: 5)

Oligonucleotide 6:    CCACCTACAGACTCTTTACG   (SEQ ID NO: 6)

Oligonucleotide 7:    CTGGGCGTAAAGAGTCTGTA   (SEQ ID NO: 7)

Oligonucleotide 8:    TGGGCGTAAAGAGTCTGTAG   (SEQ ID NO: 8)

Oligonucleotide 9:    GGGCGTAAAGAGTCTGTAGG   (SEQ ID NO: 9)

Oligonucleotide 10:   GGCGTAAAGAGTCTGTAGGT   (SEQ ID NO: 10)

Oligonucleotide 11:   GCGTAAAGAGTCTGTAGGTG   (SEQ ID NO: 11)

Oligonucleotide 12:   CGTAAAGAGTCTGTAGGTGG   (SEQ ID NO: 12)

Example 2

Identification of Bacteria Belonging to *Leptospirillum* Genus in a Metagenomic Sample The reference database was searched looking for said 12 oligonucleotides designed in Example 1, and the following Sensitivity and Selectivity values were obtained:

TABLE 1

| Oligo | N | T | R | Sensitivity | Selectivity | Rate |
|---|---|---|---|---|---|---|
| 1 | 54 | 37 | 44 | 84.1% | 68.5% | 57.6% |
| 2 | 68 | 37 | 44 | 84.1% | 54.4% | 45.8% |
| 3 | 66 | 37 | 44 | 84.1% | 56.1% | 47.1% |
| 4 | 58 | 37 | 44 | 84.1% | 63.8% | 53.6% |
| 5 | 57 | 37 | 44 | 84.1% | 64.9% | 54.6% |
| 6 | 56 | 37 | 44 | 84.1% | 66.1% | 55.6% |

TABLE 1-continued

| Oligo | N | T | R | Sensitivity | Selectivity | Rate |
|---|---|---|---|---|---|---|
| 7 | 54 | 37 | 44 | 84.1% | 68.5% | 57.6% |
| 8 | 68 | 37 | 44 | 84.1% | 54.4% | 45.8% |
| 9 | 66 | 37 | 44 | 84.1% | 56.1% | 47.1% |
| 10 | 58 | 37 | 44 | 84.1% | 63.8% | 53.6% |
| 11 | 57 | 37 | 44 | 84.1% | 64.9% | 54.6% |
| 12 | 56 | 37 | 44 | 84.1% | 66.1% | 55.6% |

N = number of sequences belonging to the target taxonomical group that are present in the evaluation database.
T = number of sequences belonging to the target taxonomical group to which said oligonucleotide hybridizes; and
R = total number of sequences to which said oligonucleotide hybridizes.

According to these results, oligonucleotides 1 and 7 were selected as best candidates. Both were synthesized, fluorescently labeled with Cy5 and used as probes to identify bacteria belonging to *Leptospirillum* genus in a metagenomic sample by using the FISH technique. To assess that what was detected corresponds only to *Leptospirillum*, controls were carried out with pure *Leptospirillum ferrooxidans* cultures, and a specific detection was found.

Example 3

Design of a Specific Oligonucleotide Pair for Bacteria Belonging to *Sulfobacillus thermosulfidooxidans* Species In the "evaluation database" obtained in Example 1, existing sequences for *Sulfobacillus thermosulfidooxidans* bacteria were selected, 8 sequences in this case, which form the "design database".

Two sets of oligonucleotides that have 19 to 21 letters present in each of the sequences were determined, discarding those sequences appearing more than once within each sequence, considering up to 3 substitutions, using Algorithm 1. All oligonucleotides with a ΔGh value lower than −1.5 kcal/mole and with a ΔGd value lower than −7 kcal/mole were discarded. The first set considers all sub-sequences with 19 to 21 nucleotides in the target sequences and the second set considers the corresponding reverse-complementary sequences. Then, oligonucleotides pairs or primers that have hybridization sites with 200-500 nucleotides between them were determined. This primer pairs were evaluated according to their thermodynamic stability using the criteria described in M. Zuker. (2003) *Mfold web server for nucleic acid folding and hybridization prediction.* Nucleic Acids Res. 31 (13), 3406-15, and all pairs having a cross hybridization energy $\Delta Gx_{min}$ lower than −12 kcal/mole were discarded. This analysis provided a total of 237,223 oligonucleotides pairs or primers that were present in the 8 sequences in the design database. These 237,223 oligonucleotides pairs or primers constitute the "candidate oligonucleotides pairs or primers" designed by the method.

For each of these pairs the taxonomical specificity was evaluated in terms of their "Sensitivity", "Selectivity" and "Rate" indexes. The first 5 primer pairs selected according to these criteria are shown in Table 2

TABLE 2

| | Sense Primer | Antisense Primer |
|---|---|---|
| Pair 1 | GCTTGGCAACAGGCGCTCA (SEQ ID NO: 13) | GGCTTCCTCCGTCGGTACCG (SEQ ID NO: 14) |
| Pair 2 | TGAGTGGGGGATATCGGGCC (SEQ ID NO: 15) | TTTGCAGGGGCTTCCTCCGT (SEQ ID NO: 16) |
| Pair 3 | AGGCGCTCACAGGGGAGCTC (SEQ ID NO: 17) | GCGGCTGCTGGCACGTAGTT (SEQ ID NO: 18) |
| Pair 4 | GGTGAGGAACACGTGAGTG (SEQ ID NO: 19) | CCGGAGGCTTAAAACCGCT (SEQ ID NO: 20) |
| Pair 5 | CGGGCTGTGAGTGGGGGAT (SEQ ID NO: 21) | GGGGCTTCCTCCGTCGGTA (SEQ ID NO: 22) |

Example 4

Other Results

Primer Design for Different Taxons.

The described method has been used for the design of many primer pairs specific for different taxons, like *Acidithiobacillus thiooxidans*, *Acidithiobacillus ferrooxidans*, *Leptospirillum* sp., *Acidiphillum* sp. In Table 3 thermodynamic and specificity requirements are shown corresponding to 4 oligonucleotides pairs or primers that were designed using the method of the invention to perform a specific PCR for each microorganism indicated in said Table, namely *A. ferrooxidans*, *A. thiooxidans*, *Leptospirillum* sp. y *Acidiphillum* sp. These oligonucleotides are useful as PCR primers for said taxons.

Table 4 shows sequences of selected specific primers.

TABLE 3

| Sense | | | Antisense | | | | Size | | Dimer | Specificity | | | | |
|---|---|---|---|---|---|---|---|---|---|---|---|---|---|---|
| Primer | $T_m$ | $\Delta G_d$ | $\Delta G_h$ | Primer | $T_m$ | $\Delta G_d$ | $\Delta G_h$ | Min | Max | $\Delta G_x$ | Sensit | Select | Rate | Org | Sp |
| *A. ferrooxidans* Primers | | | | | | | | | | | | | | | |
| TH674.5F | 62 | −3.44 | 1.53 | TH1116.11R | 60 | −3.23 | 0.57 | 444 | 444 | −9.98 | 4.00 | 100.00 | 4.00 | 1 | 1 |
| *A. thiooxidans* Primers | | | | | | | | | | | | | | | |
| TH1143.9F | 68 | −2.84 | −0.79 | TH1393.1R | 62 | −2.18 | 0.36 | 250 | 250 | −7.53 | 20.00 | 100.00 | 20.00 | 1 | 1 |
| *Leptospirillum* sp. Primers | | | | | | | | | | | | | | | |
| LP1233.1F | 60 | −4.49 | 1.07 | LP1472.1R | 58 | −4.88 | 1.47 | 241 | 241 | −11.38 | 18.18 | 100.00 | 18.18 | 8 | 8 |
| *Acidiphillum* sp. Primers | | | | | | | | | | | | | | | |
| AP202.6F | 62 | −2.65 | 1.40 | AP626.2R | 62 | −2.27 | −1.18 | 373 | 373 | −11.27 | 2.63 | 100.00 | 2.63 | 1 | 1 |

TABLE 4

| Primer | Sequence | |
|---|---|---|
| TH674.5F | GAATTCCAGGTGTAGCGGTG | (SEQ ID NO: 23) |
| TH1116.11R | AACCGCTGCAACTAAGGACA | (SEQ ID NO: 24) |
| TH1143.9F | GGGACTCAGTGGAGACCGCC | (SEQ ID NO: 25) |
| TH1393.1R | GTGTGACGGGCGGTGTGTA | (SEQ ID NO: 26) |
| LP129.4F | GATCTGCCCTGGAGATGGGG | (SEQ ID NO: 27) |
| LP381.1R | CGTTGCTGCGTCAGGGTTG | (SEQ ID NO: 28) |
| AP112.1F | GGTGAGTAACGCGTAGGAA | (SEQ ID NO: 29) |
| AP363.1R | TCGCCCATTGTCCAATATT | (SEQ ID NO: 30) |

Design of specific primers for *A. thiooxidans* useful in a metagenomic sample.

In other study, the method of the present invention was used to design specific primers for *Acidithiobacillus thiooxidans* to be used in a metagenomic sample. Primer pairs were designed using the described method and the 4 primer pairs having the best "Rate" indexes were selected. PCR tests were carried out using 16S rDNA from 5 *Acidithiobacillus ferrooxidans* samples and 2 *Acidithiobacillus thiooxidans* samples, which were amplified using each designed primer pair.

PCR protocol used was as follows:
1. −95° C. for 5 minutes
2. −95° C. for 30 seconds
3. −62° C. for 30 seconds
4. −72° C. for 20 seconds
5. − go to step (2) 29 more times
6. −10° C. until tubes were removed FIG. 1 shows PCR results, the lanes in FIG. 1 having the following load:

TABLE 5

| Lane | Sample |
|---|---|
| 1 | *A. ferrooxidans* DSM 16786 |
| 2 | *A. ferrooxidans* ATCC23270 |
| 3 | *A. ferrooxidans* DSM 14882 |
| 4 | *A. ferrooxidans* ATCC 19859 |
| 5 | *A. ferrooxidans* ATCC33020 |
| 6 | *A. thiooxidans* sp. |
| 7 | *A. thiooxidans* DSM 504 |
| (−) | Sterile water |

As can be appreciated in FIG. 1, all the designed primer pairs amplified *A. thiooxidans*, whereas primer Pair C specifically amplifies *A. thiooxidans*, with no amplification of *A. ferrooxidans*. This means that Pair C could allow the specific determination of the presence of *A. thiooxidans* in a metagenomic sample, even when *A. ferrooxidans* is present in said sample, as is usually the case.

What is claimed is:

1. Method for the design of oligonucleotides that can be used in molecular biology procedures, for identification of a metagenomic sample wherein it comprises the steps of
   (a) building a reference sequence database from a metagenomic sample;
   (b) selecting a subset of sequences (target sequences) corresponding to target organisms, according to taxonomic classification to build a design database;
   (c) selecting candidate oligonucleotides from the target sequences in the design database, by considering all subsequences of a defined length, between 18 and 50 nucleotides, present in the target sequences and their reverse-complementary sequences;
   (d) depurating these candidate oligonucleotides according to hybridization specificity and thermodynamic stability criteria, wherein the thermodynamic stability criteria are:
      i. only sequences forming a secondary structure with a Gibbs free energy difference threshold of at least −7 kcal/mole are considered valid; and
      ii. only sequences hybridizing with a copy of itself with a Gibbs free energy difference threshold of at least −7 kcal/mole are considered valid; and
      wherein the following criteria of specificity in hybridization are considered:
      iii. oligonucleotides designed according to taxonomic specificity are selected by looking for the designed oligonucleotide in the database of step (a) and registering the number of sequences belonging to each taxonomical group to which said oligonucleotide hybridizes in a list; or
      iv. oligonucleotides designed according to oligonucleotide sensitivity under consideration with respect to the group of target sequences are selected, wherein the sensitivity corresponds to a ratio between target sequences that were found and target sequences that exist in the design database; or
      v. oligonucleotides designed according to oligonucleotide selectivity under consideration with respect to the group of target sequences are selected, wherein the selectivity corresponds to a proportion of target sequences that were found belonging to the target taxon; or
      vi. oligonucleotides designed according to a product of the sensitivity multiplied by the selectivity of the oligonucleotide under consideration with respect to the group of target sequences, being selected those oligonucleotides where the product is higher than 50% of a maximum value among all of the oligonucleotides under consideration;
   (e) obtaining the list of oligonucleotides that fulfill requirements of step (d);
   (f) producing materially, by chemical synthesis, the designed oligonucleotides; and
   (g) selecting the oligonucleotides which comply with the requirements of the desired process.

2. Method according to claim 1, wherein the subset of selected sequences in step (b) correspond to genes present in the target organisms (target genes).

3. Method according to claim 1, wherein, during the depuration of candidate oligonucleotides on step (d), an oligonucleotide is considered to be valid only when said oligonucleotide appears less than twice within each target sequence.

4. Method according to claim 3, wherein an oligonucleotide is considered to appear more than once if the same sequence is repeated or if the major part of the nucleotides belonging to two possible sequences is coincident.

5. Method according to claim 4, wherein the number of coincident oligonucleotides is 85% of the sequence or more.

6. Method according to claim 1, wherein the Gibbs free energy difference threshold is preferably −1,5 kcal/mole.

7. Method according to claim 1, further comprising labeling the oligonucleotides selected in step (g) and using said labeled oligonucleotides to identify the presence of microorganisms that belong to the target taxon in a metagenomic sample.

8. Method for the design of oligonucleotides pairs or primers that can be used in molecular biology procedures, wherein it comprises the steps of:
   (a) building a reference sequence database from a metagenomic sample;
   (b) selecting a subset of sequences corresponding to target organisms (target sequences), according to taxonomic classification to build a design database;
   (c) selecting two sets of candidate oligonucleotides from the design database, wherein the first set considers all subsequences of a defined length, between 18 and 50 nucleotides, present in the target sequences and the second set considers the corresponding reverse-complementary sequences, wherein each candidate oligonucleotide is evaluated thermodynamically, according to the following criteria:
      i. only sequences forming a secondary structure with a Gibbs free energy difference threshold of at least −7 kcal/mole are considered valid; and
      ii. only sequences hybridizing with a copy of itself with a Gibbs free energy difference threshold of at least −7 kcal/mole are considered valid; and
      a set of pairs of oligonucleotides formed by an element of each established set is selected, considering the distance between the position of hybridization of the first and second oligonucleotide in a determined sequence is in a pre-established range;
   (d) obtaining a list of pairs of oligonucleotides formed by one element of each set satisfying the physic and thermodynamic conditions, where these are the candidate oligonucleotides, and depurating these pairs of candidate oligonucleotides according to hybridization specificity and thermodynamic stability criteria, wherein the thermodynamic stability criteria are:
      i. the selection of a set of oligonucleotides pairs or primers formed by one element from each set established on step (c) considers that the difference between the predicted melting temperatures (Tm) for both oligonucleotides is within a range of less than 4° C.; and ii. the selection of a set of oligonucleotides pairs or primers formed by one element from each set established on step (c) considers that the most stable structure that could be formed by both oligonucleotides has a Gibbs free energy difference of at least −12 kcal/mole;

wherein the following specificity criteria are considered in the hybridization:

iii. pairs of oligonucleotides designed according to taxonomic specificity are selected by intersecting the sets of sequences in which each of the oligonucleotides of the pair hybridize in the database of step (a); or iv. pairs of oligonucleotides designed according to oligonucleotide sensitivity in consideration with respect to the group of target sequences are selected, wherein the sensitivity corresponds to a ratio between target sequences where both oligonucleotides hybridize and target sequences that exist in the design database; or v. pairs of oligonucleotides designed according to oligonucleotide selectivity in consideration with respect to the group of target sequences are selected, wherein the selectivity corresponds to a proportion of target sequences where both oligonucleotides belonging to the target taxon hybridize and the number of total sequences where both oligonucleotides hybridize; or vi. pairs of oligonucleotides designed according to the product of the sensitivity multiplied by the selectivity of the pairs of oligonucleotides under consideration with respect to the group of target sequences, being selected those oligonucleotides where the product is higher than 50% of a maximum value among all of the pairs of oligonucleotides under consideration;

(e) obtaining a list of oligonucleotides that fulfill the requirements of step (d), which constitute the oligonucleotides designed by the method;

(f) producing materially, by chemical synthesis, the designed oligonucleotides; and (g) selecting the oligonucleotides which comply with the requirements of the desired process.

9. Method according to claim 8, wherein the subset of selected sequences in step (b) corresponds to target genes.

10. Method according to claim 8, wherein, during the depuration of candidate oligonucleotides on step (d), an oligonucleotide is considered to be valid only when said oligonucleotide appears less than twice within each target sequence.

11. Method according to claim 10, wherein an oligonucleotide is considered to appear more than once if the same sequence is repeated or if the major part of the nucleotides belonging to two possible sequences is coincident.

12. Method according to claim 11, wherein the number of coincident oligonucleotides is 85% of the sequence or more.

\* \* \* \* \*

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tacagactct ttacgcccag          20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
ctacagactc tttacgccca          20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
cctacagact ctttacgccc          20

<210> SEQ ID NO 4

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 4
acctacagac tctttacgcc                                                   20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
cacctacaga ctctttacgc                                                   20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
ccacctacag actctttacg                                                   20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide

<400> SEQUENCE: 7
ctgggcgtaa agagtctgta                                                   20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide

<400> SEQUENCE: 8
tgggcgtaaa gagtctgtag                                                   20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
gggcgtaaag agtctgtagg                                                   20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide

<400> SEQUENCE: 10
```

-continued ggcgtaaaga gtctgtaggt                               20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
gcgtaaagag tctgtaggtg                               20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
cgtaaagagt ctgtaggtgg                               20

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide

<400> SEQUENCE: 13
gcttggcaac aggcgctca                                19

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
ggcttcctcc gtcggtaccg                               20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide

<400> SEQUENCE: 15
tgagtggggg atatcgggcc                               20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
tttgcagggg cttcctccgt                               20

<210> SEQ ID NO 17
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 17
aggcgctcac agggagctc                                                    20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide

<400> SEQUENCE: 18
gcggctgctg gcacgtagtt                                                   20

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide

<400> SEQUENCE: 19
ggtgaggaac acgtgagtg                                                    19

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
ccggaggctt aaaaccgct                                                    19

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide

<400> SEQUENCE: 21
cgggctgtga gtgggggat                                                    19

<210> SEQ ID NO 22
<211> LENGTH: 19
<212> TYPE: DNA
<213> ORGANISM: Artificial Sequence
<220> FEATURE:
<223> OTHER INFORMATION: Oligonucleotide

<400> SEQUENCE: 22
ggggcttcct ccgtcggta                                                    19

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide

<400> SEQUENCE: 23
gaattccagg tgtagcggtg                                                   20
```

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide

<400> SEQUENCE: 24
aaccgctgca actaaggaca                                                    20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
gggactcagt ggagaccgcc                                                    20

<210> SEQ ID NO 26
<211> LENGTH: 19
<212> TYPE: DNA
<213> ORGANISM: Artificial Sequence
<220> FEATURE:
<223> OTHER INFORMATION: Oligonucleotide

<400> SEQUENCE: 26
gtgtgacggg cggtgtgta                                                     19

<210> SEQ ID NO 27
<211> LENGTH: 20
<212> TYPE: DNA
<213> ORGANISM: Artificial Sequence
<220> FEATURE:
<223> OTHER INFORMATION: Oligonucleotide

<400> SEQUENCE: 27
gatctgccct ggagatgggg                                                    20

<210> SEQ ID NO 28
<211> LENGTH: 19
<212> TYPE: DNA
<213> ORGANISM: Artificial Sequence
<220> FEATURE:
<223> OTHER INFORMATION: Oligonucleotide

<400> SEQUENCE: 28
cgttgctgcg tcagggttg                                                     19

<210> SEQ ID NO 29
<211> LENGTH: 19
<212> TYPE: DNA
<213> ORGANISM: Artificial Sequence
<220> FEATURE:
<223> OTHER INFORMATION: Oligonucleotide

<400> SEQUENCE: 29
ggtgagtaac gcgtaggaa                                                     19

<210> SEQ ID NO 30
<211> LENGTH: 19
<212> TYPE: DNA
<213> ORGANISM: Artificial Sequence
<220> FEATURE:

```
<223> OTHER INFORMATION: Oligonucleotide

<400> SEQUENCE: 30
tcgcccattg tccaatatt                                              19
```